(12) United States Patent
Ricco et al.

(10) Patent No.: US 10,905,324 B2
(45) Date of Patent: Feb. 2, 2021

(54) SPATIAL SUPER-RESOLUTION APPARATUS FOR FLUORESCENCE ANALYSIS OF EYE FUNDUS

(71) Applicant: CRESTOPTICS S.p.A., Rome (IT)

(72) Inventors: Vincenzo Ricco, Rome (IT); Raino Ceccarelli, Rome (IT); Andrea Latini, Rome (IT)

(73) Assignee: CRESTOPTICS S.P.A., Rome (IT)

( * ) Notice: Subject to any disclaimer, the term of this patent is extended or adjusted under 35 U.S.C. 154(b) by 93 days.

(21) Appl. No.: 16/461,359

(22) PCT Filed: Nov. 21, 2017

(86) PCT No.: PCT/IB2017/057284
§ 371 (c)(1),
(2) Date: May 15, 2019

(87) PCT Pub. No.: WO2018/092109
PCT Pub. Date: May 24, 2018

(65) Prior Publication Data
US 2019/0320894 A1  Oct. 24, 2019

(30) Foreign Application Priority Data
Nov. 21, 2016 (IT) .............. 1020160117339

(51) Int. Cl.
| | |
|---|---|
| *A61B 3/125* | (2006.01) |
| *A61B 3/00* | (2006.01) |
| *A61B 3/13* | (2006.01) |
| *A61B 3/14* | (2006.01) |
| *G02B 21/00* | (2006.01) |
| *G02B 21/36* | (2006.01) |

(52) U.S. Cl.
CPC ............ *A61B 3/125* (2013.01); *A61B 3/0083* (2013.01); *A61B 3/13* (2013.01); *A61B 3/14* (2013.01); *G02B 21/0076* (2013.01); *G02B 21/361* (2013.01)

(58) Field of Classification Search
CPC ......... A61B 3/125; A61B 3/0083; A61B 3/13; A61B 3/14; G02B 21/0076; G02B 21/361
USPC ....................... 351/205, 206, 246
See application file for complete search history.

(56) References Cited

U.S. PATENT DOCUMENTS

| | | | |
|---|---|---|---|
| 8,616,702 B2 * | 12/2013 | Abramoff | ............ A61B 3/1225 351/206 |
| 10,244,940 B2 | 4/2019 | Bublitz et al. | |
| 2012/0069299 A1 | 3/2012 | Abrámoff | |

FOREIGN PATENT DOCUMENTS

| | | |
|---|---|---|
| CN | 105615824 A | 1/2016 |
| WO | 2016137396 A1 | 9/2016 |

OTHER PUBLICATIONS

International Search Report for application PCT/IB2017/057284, dated Mar. 14, 2018, 3 pages.

* cited by examiner

*Primary Examiner* — James R Greece
(74) *Attorney, Agent, or Firm* — Loza & Loza, LLP

(57) ABSTRACT

Fluorescence microscopy apparatus for the analysis of a fundus of a sample eye, based on the use of an optical equipment configured to generate a Bessel beam inside a sample eye and an objective configured to increase the numerical aperture of an "objective-cornea-lens" assembly by reducing the overall focal length of the fluorescence microscopy apparatus, also allowing a significant increase in spatial resolution compared to conventional microscopy systems.

20 Claims, 8 Drawing Sheets

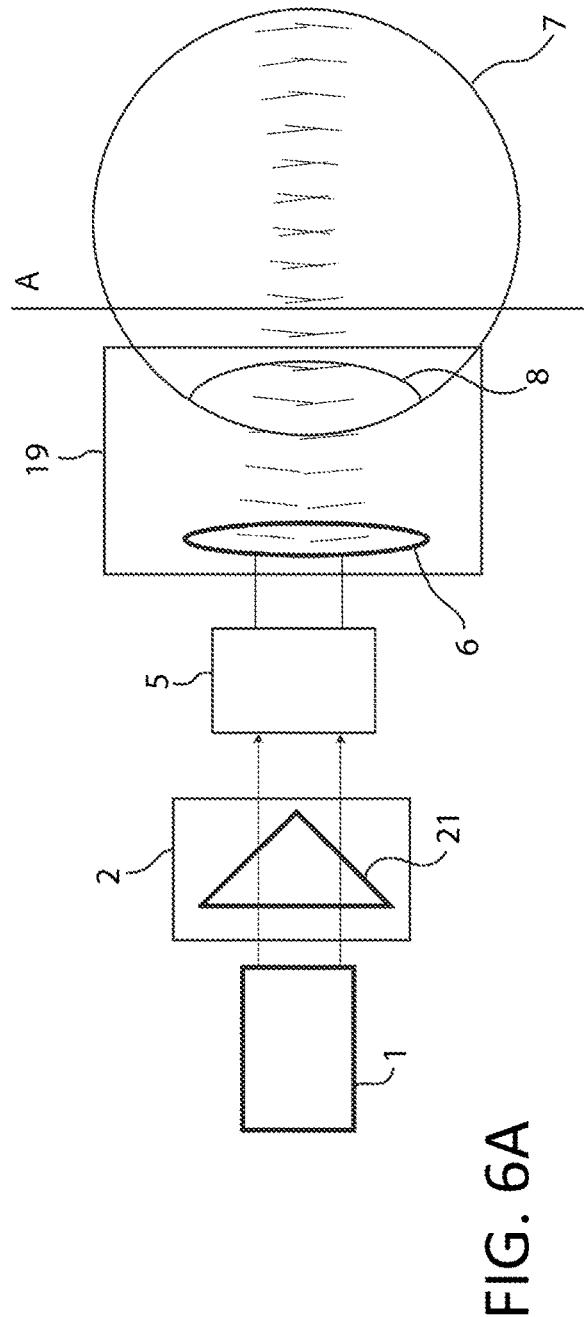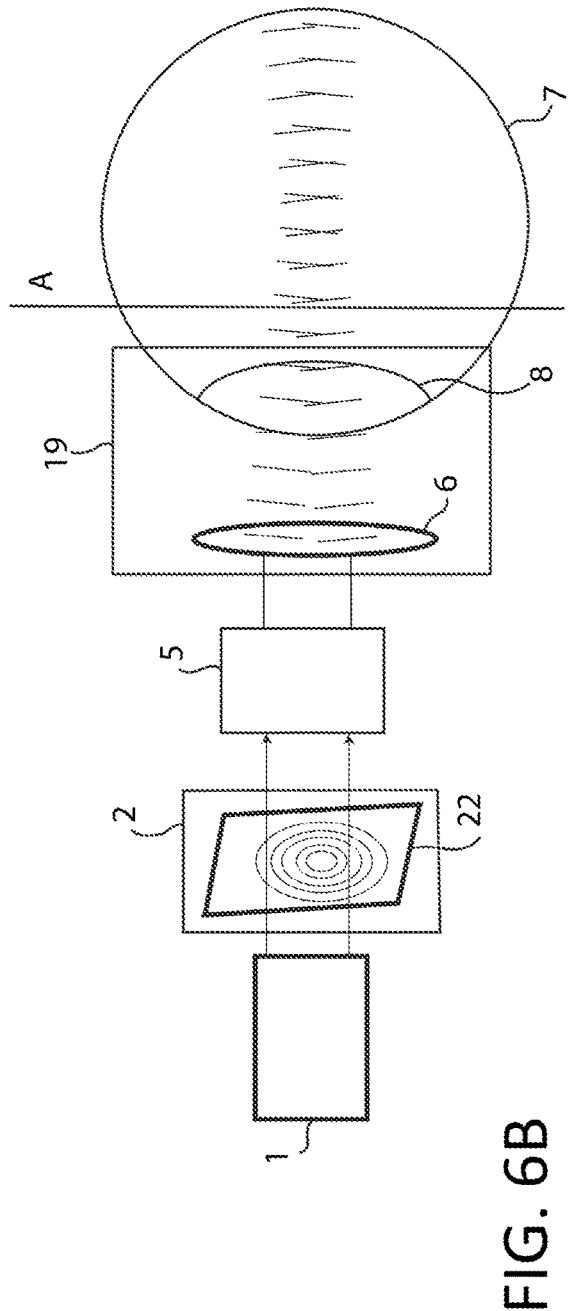
FIG. 6A
FIG. 6B

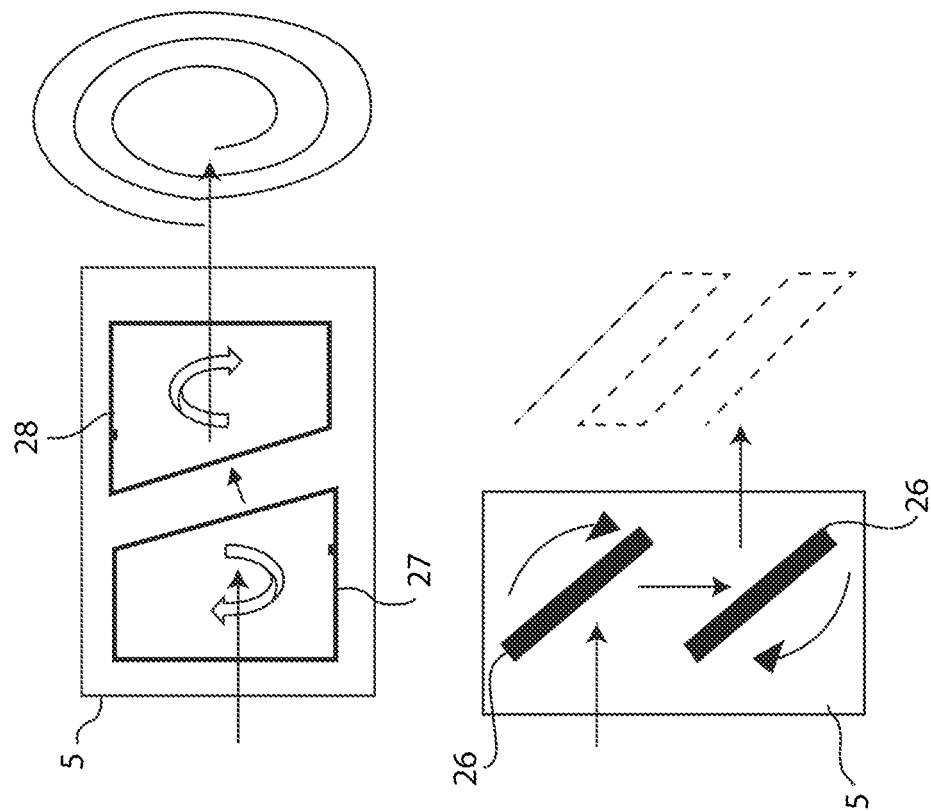

SPATIAL SUPER-RESOLUTION APPARATUS FOR FLUORESCENCE ANALYSIS OF EYE FUNDUS

The present invention concerns fluorescence microscopy for eye fundus analysis for diagnostic purposes, and refers to a microscopy apparatus based on the use of a Bessel beam. This fluorescence microscopy apparatus allows to excite the eye fundus and to detect with spatial super-resolution the fluorescence signals at the eye fundus, not to limit the numerical aperture of the scanning beam and to greatly reduce the noise in the acquired images, in particular the level of background noise due to the autofluorescence of the intraocular tissues with respect to the signal associated with markers usable for identifying proteins, or other specific molecules to be found in the retina of the eye, consequently increasing the resolution of acquired images in a simple, efficient, reliable, and inexpensive way.

In the last decades fluorescence microscopy, also called dark field microscopy, has become a fundamental tool for researching activities in the biological field. The use of synthetic dyes and, subsequently, of green fluorescent proteins or GFP has allowed to visualise with high resolution the inside of the cells both for morphological and functional analyses, since the GFP allow also in vivo fluorescence microscopy.

Confocal techniques, mainly confocal laser scanning microscopy (CLSM) and spinning disk confocal microscopy (SDCM), and super-resolution techniques, such as structured light microscopy and techniques based on reduced population of fluorescent cells, such as photo-activated localization microscopy (PALM) and stochastic optical reconstruction microscopy (STORM), have allowed a further step forward, giving the possibility of improving the lateral resolution "x-y" (in the plane orthogonal to the optical axis, whereby it is assumed that the x and y axes lie in the plane of the sample) and the axial resolution "z" (along the optical axis that is orthogonal to the plane of the sample), and thus they have offered the possibility of carrying out 3D reconstructions of the cell with a very high detail level (with resolutions which can reach tens of nanometers).

However, such confocal and super-resolution techniques have some drawbacks.

First of all, the sample thickness is limited (it is generally difficult to carry out measurements on samples thicker than 20 micrometres) because of diffusion effects due to the turbidity of the sample and to fluorescence background due to the out-of-focus planes.

Also, the resolution capability of both techniques is limited by the signal-to-noise or S/N ratio, in which both the noise of the signal acquisition equipment and surrounding environment noise and the noise of fluorescence background due to out-of-focus planes and sample turbidity contribute to the total noise. In particular, this ratio limits the use of high orders in the polynomials which form the deconvolution algorithm used in the structured light super-resolution methods.

Moreover, since the signal of the fluorescence of the out-of-focus planes has the same dependency of the signal of interest on the excitation light, the increase of the excitation intensity or exposure time cannot improve performance beyond the limit due to the saturation of the acquisition sensor, e.g. a CCD or sCMOS (scientific CMOS) sensor.

In this context, the solution proposed according to the present invention is introduced allowing to solve the aforementioned problems of the prior art solutions.

Therefore, it is an object of the present invention to increase the penetration capability of a fluorescence microscopy apparatus for examining a thick sample as the eye, to increase the spatial resolution and to improve the signal-to-noise ratio in a simple, efficient, reliable, and inexpensive way.

It is specific subject matter of the present invention a fluorescence microscopy apparatus for analysing a fundus of a sample eye of a patient comprising:

- a generation optical unit configured to receive a basic light beam from a first light source and to generate an excitation light beam;
- a scanning system configured to receive the excitation light beam from the generation optical unit and to make the excitation light beam scan at least one portion of the fundus of the sample eye;
- an optical launch unit configured to receive the excitation light beam from the scanning system and to at least partially collimate an isotropic radiation of fluorescent molecules of the sample eye in a fluorescence beam, the optical launch unit comprising an objective having a focal length $f_{obj}$ and an optical power $K_{obj}$ equal to $$K_{obj} = 1/f_{obj}$$

where n is a refractive index of the medium;
- a patient's head supporting and positioning unit configured to support the head with cornea and lens of the sample eye facing the optical launch unit and to position the sample eye in a launch position at a distance d from the objective, wherein in the launch position the optical launch unit and cornea and lens of the sample eye form an optical launch assembly having an effective optical power $K_{eff}$ equal to $$K_{eff} = 1/f_{eff} = K_{obj} + K_{eye} - \frac{d}{n_i} \cdot K_{obj} \cdot K_{eye}$$

where $f_{eff}$ is an effective focal length of the optical launch assembly, $K_{eye}$ is a constant optical power contribution, $n_i$ is a refractive index of the medium between sample eye and objective;
- a sensor device configured to detect the fluorescence beam coming from the optical launch unit;
- one or more optical components configured to transmit said excitation light beam coming from the generation optical unit to the scanning system and to transmit said fluorescence beam from the optical launch unit and coming from the scanning system to the sensor device;

wherein when said patient's head supporting and positioning unit positions the sample eye in the launch position, said optical launch assembly formed by the optical launch unit and the cornea and lens of the sample eye is configured to send the excitation light beam on said at least one portion of the fundus of the sample eye, and the generation optical unit is configured to generate an excitation light beam having phase relationships configured to compose said excitation light beam, after having passed through the optical launch assembly, in a Bessel beam inside the sample eye in correspondence of a plane orthogonal to an optical propagation axis, wherein said plane is between the lens of the sample eye and said at least one portion of the fundus of the sample eye, the focal length $f_{obj}$ of the objective satisfying the condition that an effective numerical aperture $NA_{eff}$ of said optical launch assembly, given by $$NA_{eff} = n_{eye} \cdot \sin(R_{eye}/f_{eff})$$

is not lower than 0.9, where $n_{eye}$ is a refractive index of the sample eye and $R_{eye}$ is the radius of the sample eye.

According to an additional aspect of the invention, when said patient's head supporting and positioning unit positions the sample eye in the launch position, the distanced of the sample eye from the objective may be not longer than 20 mm, optionally not longer than 10 mm, more optionally not longer than 5 mm, still more optionally not longer than 2 mm.

According to another aspect of the invention, said fluorescence microscopy apparatus may include at least one first narrowband cleaning filter configured to eliminate a spurious fluorescence background from the excitation light beam.

According to a further aspect of the invention, said objective may be a single or double adaptive lens, optionally an adaptive contact lens whereby the distanced of the sample eye from the objective is zero.

According to an additional aspect of the invention, said fluorescence microscopy apparatus may comprise an imaging optical unit configured to focus said fluorescence beam on the sensor device.

According to another aspect of the invention, said sensor device may include a plurality of sensing elements selected from the group comprising photomultipliers, avalanche diodes, CCDs, or SCMOSs.

According to a further aspect of the invention, said fluorescence microscopy apparatus may include a plurality of microlenses placed upstream of the sensor device each one of which is biunivocally coupled to a respective element of the plurality of sensing elements of the sensor device.

According to an additional aspect of the invention, said fluorescence microscopy apparatus may include a second light source generating an additional excitation light beam configured to excite at least one additional portion of the sample eye, that internally includes said at least one portion of the sample eye scanned by the excitation light beam generated by the generation optical unit, said additional excitation light beam being configured to saturate an autofluorescence of intraocular tissues of the sample eye According to another aspect of the invention, said generation optical unit may include a static optical phase filter placed on the Fourier plane of the optical launch unit, optionally a bidimensional grating made of multiple dielectric layers, more optionally an axicon lens, still more optionally an axicon lens provided with a phase mask.

According to a further aspect of the invention, said generation optical unit may include a spatial light modulator, optionally a phase spatial light modulator or an amplitude spatial light modulator followed by a Fourier lens.

According to an additional aspect of the invention, said scanning system may include a first and a second wedges configured to independently rotate by means of two separated motors, configured to be controlled in a synchronous way, wherein the two wedges optionally have a resolution of angular position equal to at least $\frac{1}{50}$ of a degree, whereby a scanning resolution is equal to at least one microradian on a field of ±1°.

According to another aspect of the invention, said fluorescence microscopy apparatus may include a wide-field imaging system operating in near infrared (NIR) for imaging sub-retinal structures of the sample eye and an additional optical component, placed between the scanning system and the optical launch unit, said additional optical component being configured to be transparent to radiation in near infrared and to reflect the excitation light beam from the scanning system towards the optical launch unit and the fluorescence light beam from the optical launch unit towards the scanning system, the system further comprising:

a third light source configured to generate a first NIR light beam to be sent to said additional optical component;

a NIR sensor device configured to detect a second NIR light beam reflected by sub-retinal structures of the sample eye and coming from the additional optical component, optionally a CCD sensor or a SCMOS sensor, the NIR sensor device being optionally configured to operate at a frequency not lower than 100 frames/sec;

one or more NIR optical components configured to transmit said first NIR light beam from the third light source to said additional optical component and said second reflected NIR light beam coming from said additional optical component to the NIR sensor device.

According to a further aspect of the invention, said imaging system may include an imaging optical unit configured to focus the second NIR light beam on the NIR sensor device.

According to an additional aspect of the invention, said apparatus may include at least one second narrowband cleaning filter configured to eliminate a spurious fluorescence background from said first NIR light beam.

The invention is based on the use of an optical equipment for the generation of a Bessel beam placed behind an objective configured to increase the numerical aperture of an "objective-cornea-lens" assembly by reducing the overall focal length of the fluorescence microscopy.

Fundamental characteristics of a Bessel beam are its propagation devoid of divergence (at least for the path inside the human eye equal to about 24 mm), the beam diameter that can be confined in $\lambda/2$ (it depends on the numerical aperture of the optical system that generates it), where λ is the beam wavelength, the capability to regenerate after any possible interference with scattering elements such as those present in a turbid fluid. This allows to achieve significant advantages with respect to the prior art, e.g. allowing the apparatus of the present invention to have a high angular spatial resolution with which the eye fundus can be scanned and with which the presence of a fluorescence area can be angularly resolved. A further advantage of the present invention is that of allowing the attainment of a mapping of fluorescence areas and of measuring the size of said fluorescence areas, if such areas are larger than the diameter of the Bessel beam, or of defining them as sub-diffraction, i.e. equal to or lower than the beam diameter. Still another advantage of the present invention is that of allowing an angular scanning of an entire eye fundus or of an area equal to 2-3 times that of the fovea centralis.

The present invention will be now described, by way of illustration and not by way of limitation, according to its preferred embodiments, by particularly referring to the Figures of the annexed drawings, in which:

FIGS. 6 and 7 show diagrams of generation optical units of some embodiments of the fluorescence apparatus microscopy for the analysis of the eye fundus according to the invention;

FIG. 8 shows diagrams of angular scanning systems of some embodiments of the fluorescence microscopy apparatus for the analysis of the eye fundus according to the invention.

In the Figures, identical reference numerals will be used for alike elements.

Figure 1:
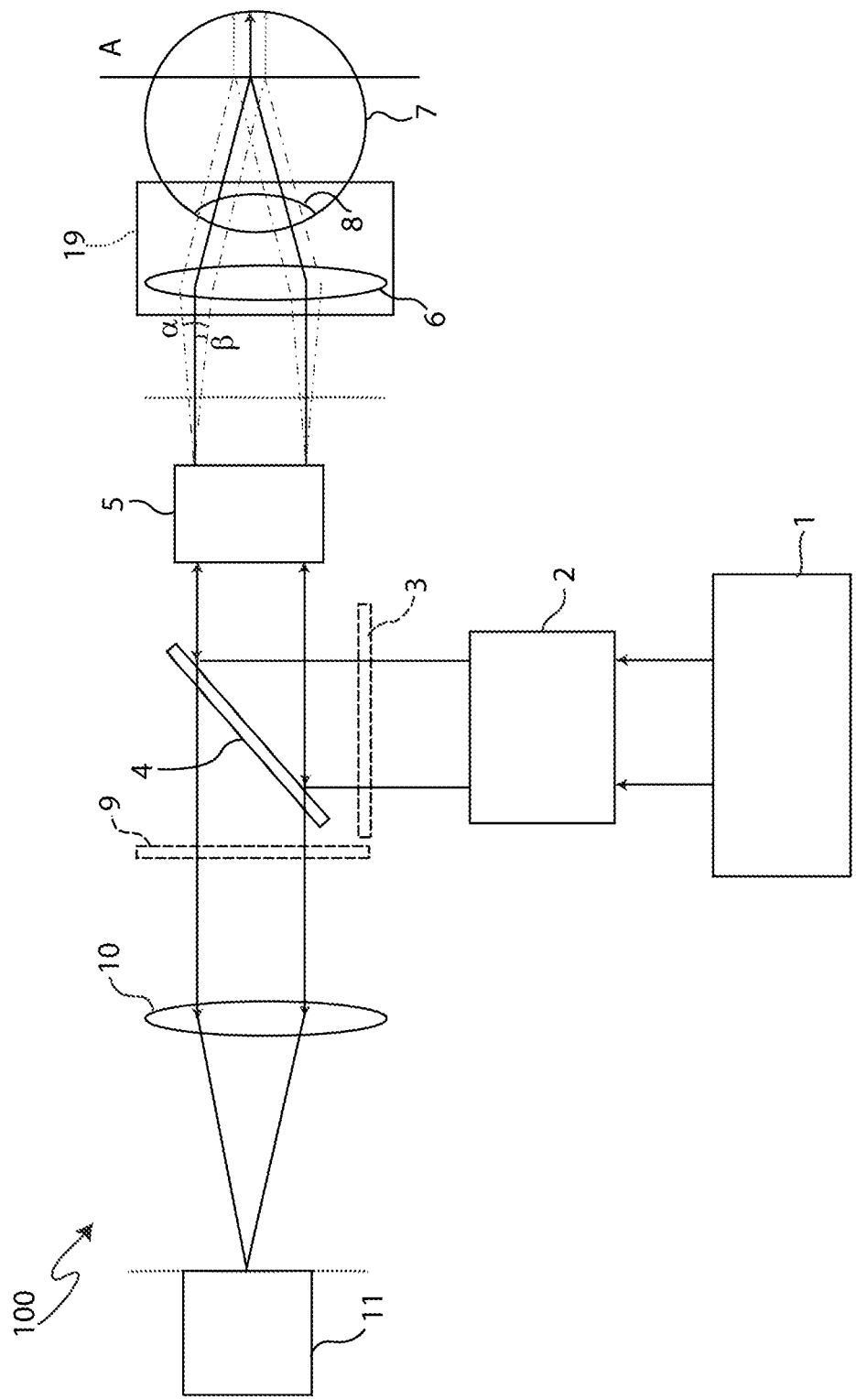
FIG. 1 shows a diagram of a first embodiment of the fluorescence microscopy apparatus for the analysis of the eye fundus according to the invention.

FIG. 1 schematically shows a first embodiment of the fluorescence microscopy apparatus for the analysis of the eye fundus according to the invention, generally indicated by the reference numeral 100. The fluorescence microscopy apparatus 100 comprises a first laser light source 1 having such wavelength λ so as to excite any fluorescent molecules present in a fundus of a sample eye 7. Through air or optical fibre, such first light source 1 sends a basic light beam to a generation optical unit 2 configured to generate a fluorescence excitation light beam with such phase relationships that, by passing through a suitable optical launch unit 19, after a few millimeters from the lens 8 of the sample eye 7 said excitation light beam will be composed in a Bessel beam (at least within a spatial range, along the optical axis, which comprises the fundus of the sample eye 7), i.e. a beam that propagates without diffraction and diffusion and that has the property of self-regenerating after interference with scattering elements, such as those that can be encountered in a turbid fluid of the sample eye 7. In particular, the excitation light beam will be composed in a Bessel beam over distances along the beam propagation axis (z-axis) longer than at least $10 \cdot z_R$, where $z_R$ is the Rayleigh length that is inversely proportional to the numerical aperture (NA) of the system:

$$z_R \propto \lambda/(\pi \cdot NA^2)$$

The excitation light beam passes through (at least) a first narrowband cleaning filter 3, configured to eliminate from the excitation light beam wavelengths due to other sources and a spurious fluorescence background that can be generated by the laser light when passing through the crossed optical components (optical fibres, lenses or other), and continues to a first dichroic filter 4 configured to reflect the excitation light beam towards a scanning system 5 configured to vary the position of the excitation light beam on a "x-y" plane orthogonal to the optical propagation axis of the excitation light beam (z-axis) and thus to perform a scanning of a plane of the fundus of the sample eye (7).

The excitation light beam emerges from the scanning system 5 and passes through the optical launch unit 19 that includes an objective with one or more optical components, configured to minimise optical aberrations; during operation of the apparatus according to the invention, i.e. when the apparatus according to the invention is applied to the sample eye 7, the optical launch unit 19 forms along with the cornea and the lens 8 of the sample eye 7 an optical launch assembly. In the preferred embodiment, the objective is an adaptive lens that may be a single or double lens (such as the one indicated by reference numeral 6 in FIG. 1), optionally an adaptive lens in contact with the sample eye 7 (such as the one indicated with the reference numeral 6' in FIG. 2). Said optical launch unit 19 is configured to compose the excitation light beam in a Bessel beam inside the sample eye 7 in correspondence of a plane A parallel to the plane "x-y" orthogonal to the optical axis "z" placed between the lens 8 and the fundus of the sample eye 7, optionally placed on the fundus of the sample eye 7.

Since the eye is assimilable to a lens usually having a focal length $f_{eye}$ equal to about 20 millimeters ($f_{eye}$=20 mm) and radius $R_{eye}$ equal to about 6 millimeters ($R_{eye}$=6 mm), whereby the eye usually has a numerical aperture $NA_{eye}$, given by the ratio between radius and focal length of this lens, equal to about 0.3 ($NA_{eye}$~0.3); actually, the human eye can also have lower values of numerical aperture, equal to about 0.2 ($NA_{eye}$~0.2). Neglecting the presence of the optical launch unit 19, the objective 6 (or 6') of which is placed at a distanced close to the cornea and lens 8 of the sample eye 7, since the transverse dimension t of a Bessel beam entering the eye is given by:

$$t = \lambda/(2 \cdot NA_{eye}) \quad [1]$$

where λ is the wavelength of the first light source 1, the values of the numerical aperture $NA_{eye}$ of the sample eye 7 would not allow to obtain a transverse resolution of the Bessel beam close to λ/2.

In order to improve this transverse resolution of the Bessel beam, the objective 6 (or 6') is placed in proximity of the eye and is configured to increase the effective numerical aperture $NA_{eff}$ of the overall system formed by the launch group and by the sample eye 7 from the value of the numeric aperture $NA_{eye}$ of the eye, as stated equal to about 0.2 ($NA_{eye}$~0.2), to a value larger than 0.9 ($NA_{eye}$>0.9). In fact, such effective numerical aperture $NA_{eye}$ is defined as $$NA_{eff} = n_{eye} \cdot \sin(R_{eye}/f_{eff}) \quad [2]$$

where n is the refractive index of the medium (i.e. of the sample eye 7), $R_{eye}$ is the radius of the sample eye 7 and $f_{eff}$ is the effective focal length of the launch assembly, formed by the optical launch unit 19 and by the cornea and lens 8 of the sample eye 7.

Such definition of the effective numerical aperture $NA_{eff}$ takes account of the advantageous mode of use wherein the radius r of the excitation light beam incident on the objective 6 (or 6') is not shorter than the radius $R_{eye}$ of the sample eye 7. However, it should be noted that, in the case where the radius r of the excitation light beam incident on the objective 6 (or 6') is shorter than the radius $R_{eye}$ of the sample eye 7, the effective numerical aperture is equal to $n_{eye} \cdot \sin(r/f_{eff})$.

Figure 2:
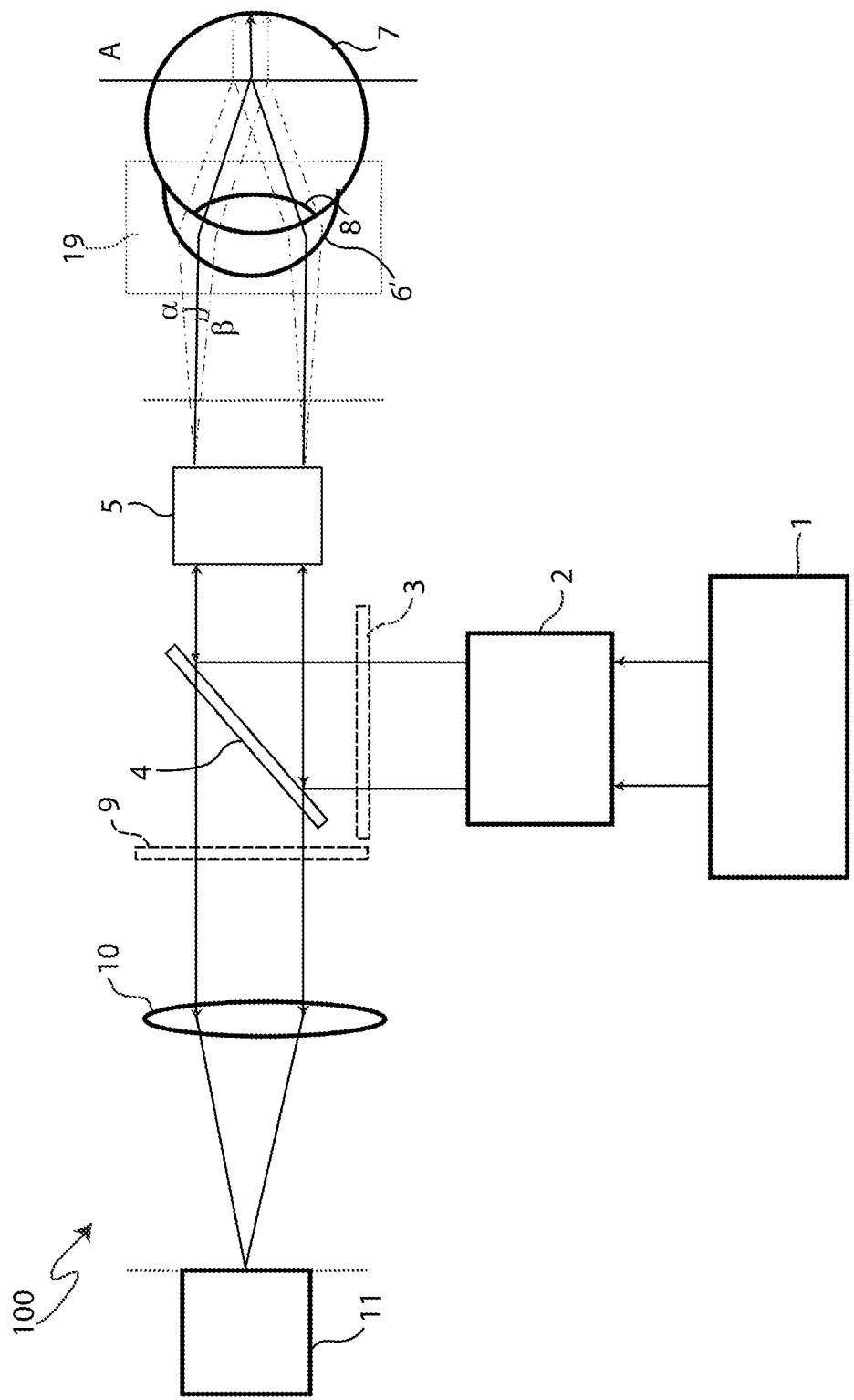
FIG. 2 shows a diagram of a second embodiment of the fluorescence microscopy apparatus for the analysis of the eye fundus according to the invention.

As known, the effective optical power $K_{eff}$ of a system comprising two thin lenses, having optical powers $K_{obj}$ and $K_{eye}$, respectively, placed at a distance d from each other, is equal to:

$$K_{eff} = K_{obj} + K_{eye} - \frac{d}{n_i} \cdot K_{obj} \cdot K_{eye} \quad [3]$$

where $$K_{eff} = 1/f_{eff} \quad [4]$$

$$K_{obj} = 1/f_{obj} \quad [5]$$

$$K_{eye} = 1/f_{eye} \quad [6]$$

and $n_i$ is the refractive index of the medium between eye sample 7 and objective 6 (or 6'); in particular, in the case of air, $n_i$ can be assumed to be equal to 1, whereas in the case of an adaptive lens 6' in contact with the sample eye 7 shown in FIG. 2, $n_i$ could be equal to the refractive index of a liquid interposed between lens 6' and sample eye 7 (however, in this case, it can be assumed that the distance d is zero, i.e. d=0, whereby the contribution $d \cdot K_{obj} \cdot K_{eye}/n_i$ is zero as well).

In particular, all the optical properties relating to the sample eye, namely focal length $f_{eye}$, radius $R_{eye}$, refraction index $n_{eye}$, and consequently numerical aperture $NA_{eye}$ and optical power $K_{eye}$ can be considered as constants, e.g. equal to an average or to limit values of a population.

Therefore, in order to make the effective numerical aperture $NA_{eff}$ given by equation [2] assume values higher than 0.9, the apparatus according to the invention positions an objective having focal length $f_{obj}$ and, consequently, optical power $K_{obj}$ at a distance d from the sample eye 7 (namely from the cornea of the sample eye 7), whereby given a distance d (or a range thereof), the value of the focal length $f_{obj}$ of the objective is determined by equation [3].

To this end, the apparatus according to the invention comprises a conventional patient's head supporting and positioning unit (not shown in the Figures) configured to support the head so that the cornea and lens 8 of the patient's sample eye 7 are facing the objective 6 (or 6') of the optical launch unit 19, and configured to position the patient's sample eye 7 in a launch position in which the sample eye 7 (namely the cornea thereof) is at a distance d from the objective 6 (or 6') of the optical launch unit 19; in this way, the optical launch unit 19 and the cornea and lens 8 of the sample eye 7 form the optical launch assembly having the effective numerical aperture $NA_{eff}$ given by equation [2]. Advantageously, when the sample eye 7 is in the launch position, the distance d of the sample eye 7 from the objective 6 (or 6') of the optical launch unit 19 is not longer than 20 mm, optionally not longer than 10 mm, more optionally not longer than 5 mm, still more optionally not longer than 2 mm (e.g., in the case of FIG. 2, the distance d is zero, i.e. d=0). By way of example, and not by way of limitation, the patient's head supporting and positioning unit may comprise a chin support and/or a patient's forehead support; optionally, one or more sensors may indicate if the patient's head is in an operative position (at which the patient's sample eye 7 is in the launch position), for example sensors selected from the group comprising or consisting of proximity sensors and contact sensors, such as photodetectors and proximity sensors.

This configuration of the launch assembly, formed by the objective 6 (or 6') of the optical launch unit 19 and by the cornea and lens 8 of the sample eye 7, allows to increase the spatial resolution of the system that depends on the diameter of the excitation light beam, potentially providing a resolution equal to $\lambda/2$ at the fundus of the sample eye 7, where X is the wavelength of the first light source 1, optionally equal to $\lambda/4$ using over-sampling techniques of a scanning and using algorithms such as the deconvolution ones applied to over-sampling. In fact, as mentioned, thanks to its non-diffractivity, a Bessel beam has a transverse dimension with respect to the propagation direction equal to about $\lambda/(2 \cdot NA)$, whereby, with a NA=1, a diameter of about $\lambda/2$ is given. Since a Bessel beam propagates without divergence and allows to reach a diameter equal to $\lambda/2$, such value is also the angular resolution $\alpha/\beta$ the plane "x-y" with which a plane of the fundus of the sample eye 7 can be scanned.

Figure 3:
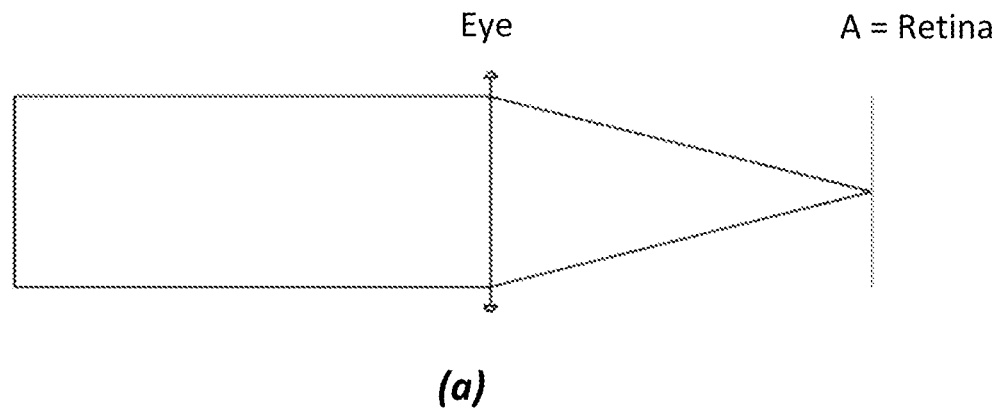
FIG. 3 shows a comparison of the different focusing modes of the beams of prior art apparatuses (FIGS. 3a and 3c) with the apparatus according to the invention (FIG. 3a)
Figure 3:
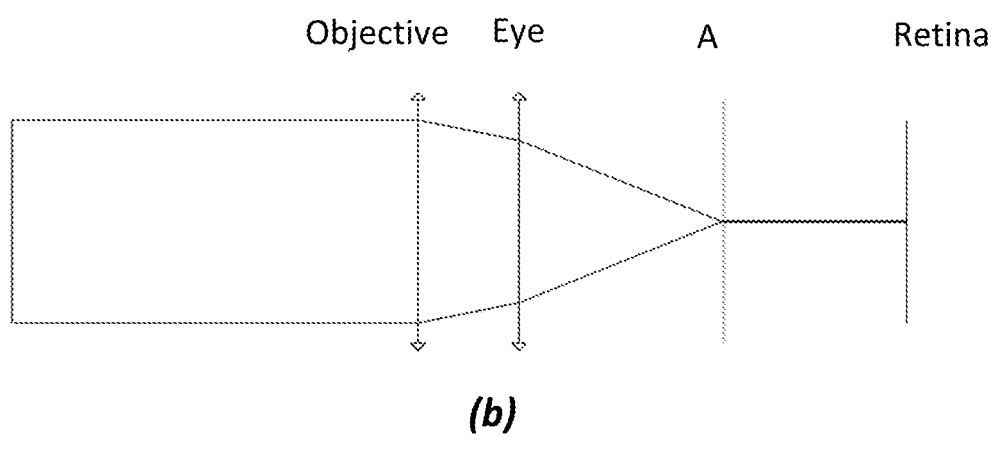
Figure 3:
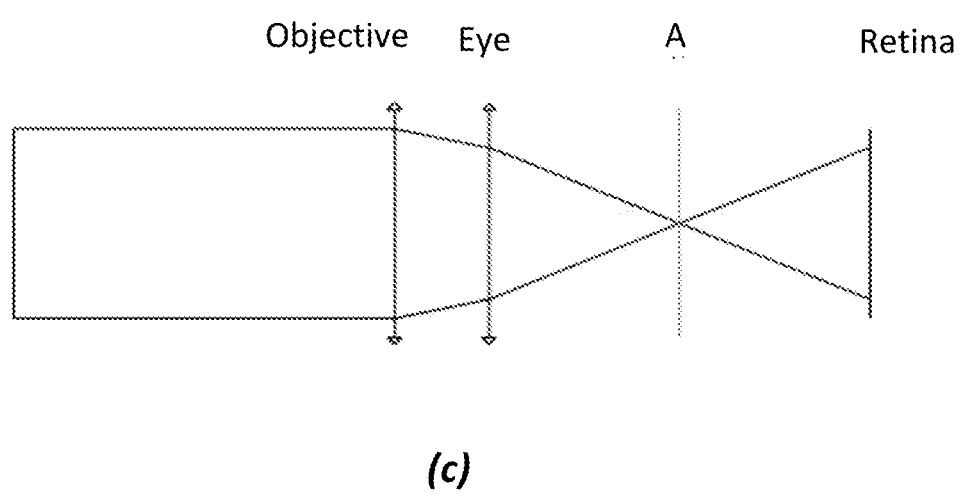

FIG. 3 shows a comparison of the different modes of focusing beams of prior art apparatuses with the apparatus according to the invention. FIG. 3a shows a schematic representation of the focusing of a (non-Bessel) excitation beam for a prior art apparatus, wherein the beam is focused on the retina of the sample eye, positioned on the focusing plane A of the optical system, and wherein the size of the excitation spot on the retina depends on the pupil size and focal length of the sample eye (assuming that the light fills the entire pupil).

FIG. 3b shows a schematic representation of the focusing of an excitation beam for the apparatus according to the invention, wherein an optical launch assembly is formed by the objective 6 (or 6') of the optical launch unit 19 and from the cornea and lens 8 of the sample eye 7 so as to focus the excitation beam on a plane A between the pupil and the retina. The excitation beam is generated so as to form a Bessel beam inside the eye, whereby the Bessel beam propagates devoid of divergence and with a diameter (and transverse resolution t) equal to $\lambda/(2*NA_{eff})$ from plane A to the retina. As mentioned, the condition $NA_{eff}>0.9$ and the distance d between objective 6 (or 6') and sample eye 7 (namely cornea of the sample eye 7), that is equal to zero in case of adaptive lens 6' in contact with the sample eye 7 and is in any case small in case of a single or double adaptive lens 6, univocally determine the properties of the objective 6 (or 6'), in particular the focal length $f_{obj}$ of the objective to be used.

FIG. 3c shows a schematic representation of the focusing of a (non-Bessel) excitation beam for a prior art apparatus wherein which the excitation beam is focused on a plane A between the pupil and the retina: it is evident that the area of the illuminated retina is definitely larger with respect to the apparatus according to the invention, with consequent loss of resolution.

In the presence of sources contained in the eye fundus, such as proteins, labeled with fluorescent molecules, such as for example curcumin (referred to herein merely by way of example), the fluorescent molecule emits an isotropic radiation, with a longer wavelength than the one of the excitation light beam, that will pass in part through the optical unit 19 emerging from it as a fluorescence light beam. It should be noted that the fluorescence light beam is substantially parallel to the excitation light beam, the illumination of the eye and the excited fluorescent beam take place along the same direction, whereby the apparatus according to the invention is based on a backscattering system, wherein illumination and detection occur along the same longitudinal axis. The first dichroic filter 4 is configured to transmit the fluorescence light beam towards an interferential emission filter 9 that allows to maximise the sensitivity of the apparatus with respect to the wavelength of the fluorescence due to specific markers with respect to the autofluorescence of the intraocular tissues and to the residual background due to scattering and/or reflections of the excitation light beam.

After having passed through the interferential emission filter 9, the fluorescence beam passes through an imaging optical unit 10 (indicated in FIGS. 1-2 and 4 as a single lens for simplicity) configured to compensate the effects of the optical unit 19 and to focus the fluorescence beam on a sensor device 11, that is configured to detect the fluorescence beam intensity for each angular position $\alpha/\beta$ at which the excitation light beam emerges from the scanning system 5 corresponding to a position x/y on the retina of the sample eye 7. An image is then obtained by composing the signals obtained on each individual position of the scanning system 5 and hence it is a numerically calculated image (for each position $\alpha/\beta$, corresponding to a position x/y of the retina, the fluorescence intensity signal is read and then a mapping of the x/y positions and intensity is executed so as to reconstruct a two-dimensional image). Such sensor device 11 can include a single sensing element, such as for instance a single photomultiplier or a single avalanche diode, or alternatively a plurality of sensing elements, such as for instance a plurality of photomultipliers or a plurality of avalanche diodes, configured to obtain information on the spatial distribution of the fluorescence beam capable to improve the resolution in a "x-y" plane and to define the longitudinal position ("z" axis) of the molecule that emitted the fluorescence through the use of algorithms borrowed from confocal microscopy.

Figure 4:
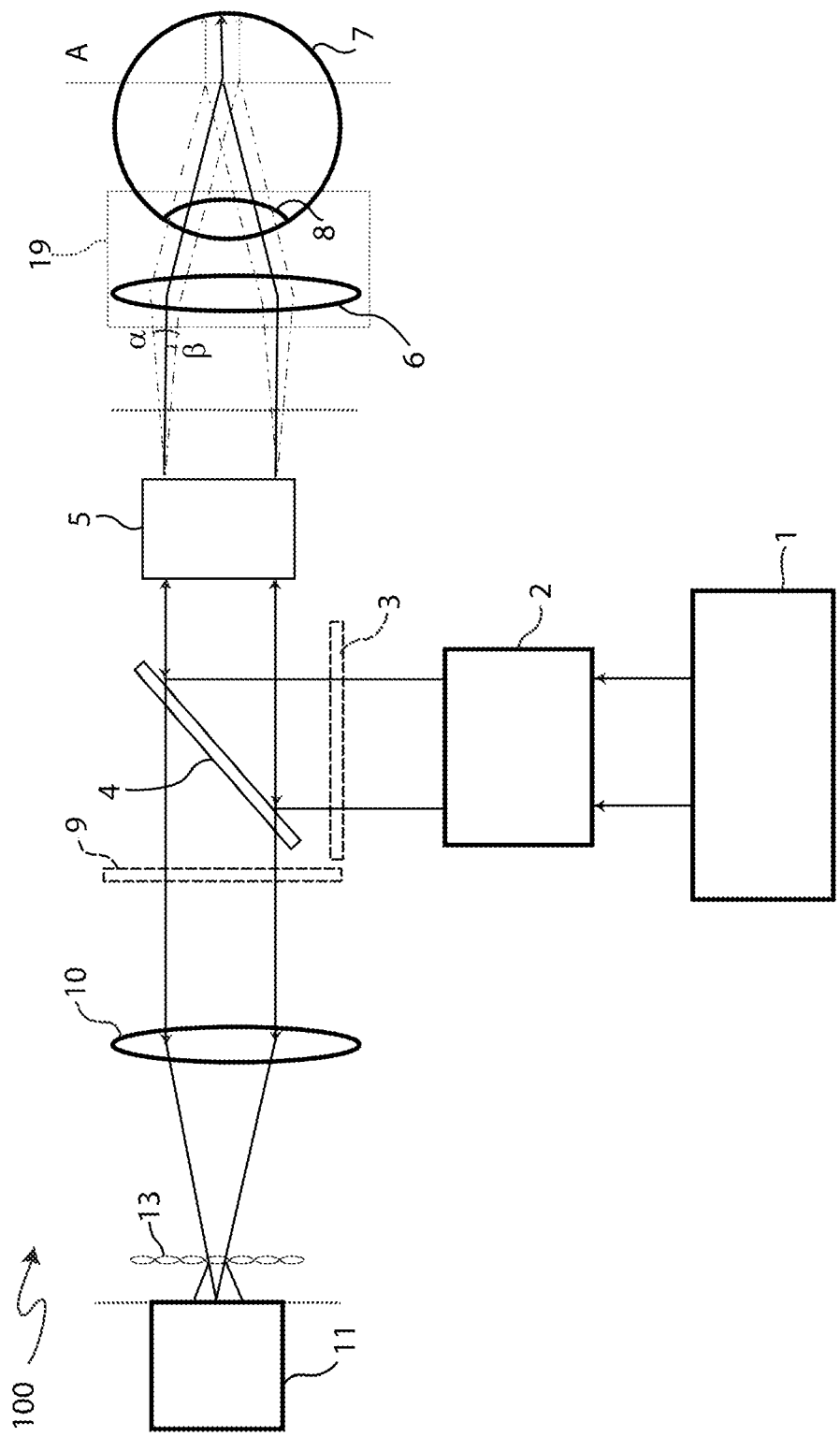
FIG. 4 shows a diagram of a third embodiment of the fluorescence microscopy apparatus for the analysis of the eye fundus according to the invention.

FIG. 4 schematically shows a third embodiment of the fluorescence microscopy apparatus according to the invention, wherein the imaging sensor 11 includes a plurality of sensing elements each of which is biunivocally coupled to a single microlens of a plurality of 13 microlenses which constitute a spatial filtering mask. Optionally, the imaging sensor 11 of the third embodiment schematically represented in FIG. 4 is made by using a CCD or SCMOS type array sensor. Said third embodiment is configured to detect fluorescence signals emitted by markers placed in the sample eye 7 in correspondence of specific positions of the "z" axis. The distribution of the light field in the Fourier plane intercepted by the plurality of microlenses or in an intermediate plane between the Fourier plane and the focal one (i.e. image plane) allows, through the Fourier analysis of the spatial frequencies or other algorithms that put in relation with one another the signal intensities of the individual sensors or the pixels of the CCD or SCMOS array, to obtain not only the fluorescence intensity information, but also the one related to the "z" position of the source, whereby the apparatus of the present invention allows to reconstruct a 3D mapping of the fluorescent molecules.

Optionally, the hereinbefore described embodiments may have a second light source (not shown in the Figures) in parallel with the first light source 1, generating an additional excitation light beam configured to excite an additional portion of the sample eye 7 that is larger than the one scanned by the excitation light beam that is composed in the Bessel beam (for example 100×100 times larger) and that includes such scanned portion, so as to saturate the autofluorescence of intraocular tissues. In fact, the autofluorescence of the intraocular tissues has a very rapid decay time compared to the one of the fluorescence of markers usable for the identification of proteins, or other specific molecules to be found in the retina, whereby a first exposure with wider field can be used to saturate the autofluorescence of a determined scanning portion and to then analyse the portion with a Bessel excitation beam in order to make a super-resolved mapping (i.e. $\lambda/2$, optionally $\lambda/4$) thereof. In other words, once it has been excited, the autofluorescence is saturated and requires a much longer regeneration time than the decay time of a marker, whereby it is possible to excite a portion with a single non-focused light pulse and to then scan the saturated portion devoid of autofluorescence with a Bessel beam. In a preferred embodiment of the present invention, the second light source parallel to the first light source 1 is periodically activated with a single pulse with a period equal to the decay time of the autofluorescence of the intraocular tissues.

Figure 5:
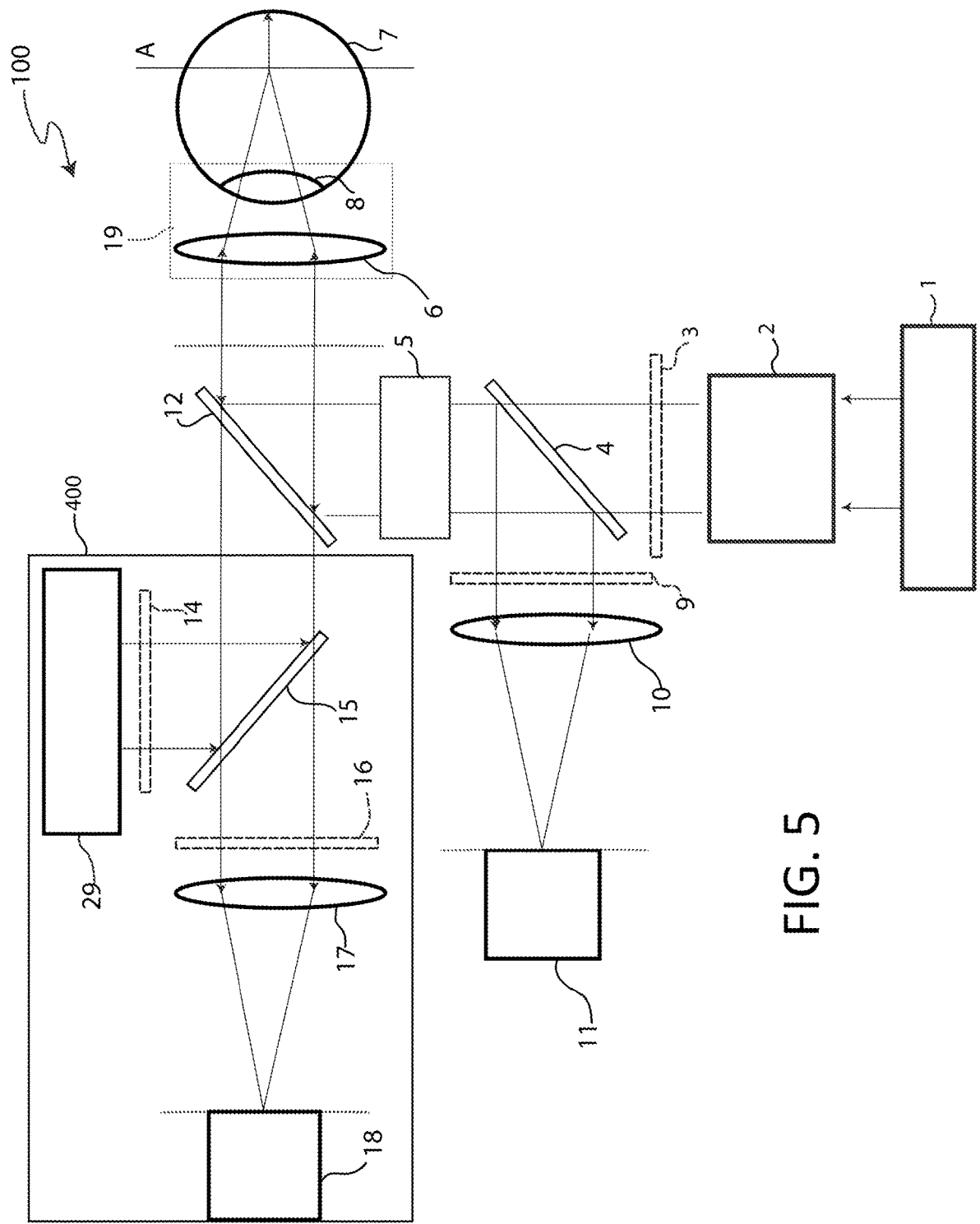
FIG. 5 shows a diagram of a fourth embodiment of the fluorescence microscopy apparatus for the analysis of the eye fundus according to the invention.

FIG. 5 schematically shows a fourth embodiment of the fluorescence microscopy apparatus according to the invention, wherein the apparatus 100' comprises a wide-field imaging system 400 operating in the near infrared (NIR) for imaging sub-retinal structures of the sample eye 7, that is configured to obtain a spatial reference for the scanning system 5, referring the position of the excitation light beam to a marking point, such as the position of the optic nerve or of an identifiable blood vessel structure of the sample eye 7. In this fourth embodiment of the present invention, the excitation light beam emerging from the scanning system 5 continues to a second dichroic filter 12 configured to reflect the excitation light beam towards the optical launch unit 19 and to reflect the fluorescence light beam emerging from the optical launch unit 19 towards the scanning system 5. The second dichroic filter 12 is also configured to transmit a first NIR light beam (i.e., in the near infrared band, having a wavelength ranging from 0.78 to 3 micrometers) emerging from the system 400 towards the sample eye 7 through the optical launch unit 19 and a second NIR light beam reflected by sub-retinal structures of the sample eye 7 and passing through the optical launch unit 19 towards the system 400.

The wide-field imaging system 400 operating in the near infrared includes a third light source 29 that generates the first NIR light beam that passes through a second cleaning filter 14 and continues to a third dichroic filter 15 configured to reflect the first NIR light beam, through the second dichroic filter 12 and the optical launch unit 19, towards the sample eye 7. Sub-retinal structures of the sample eye 7 reflect the NIR light so that a second reflected NIR light beam returns backwards, passing through the optical launch unit 19, towards the second dichroic filter 12, that transmits it to the third dichroic filter 15, that is in turn configured to transmit said second reflected NIR light beam towards a second interferential emission filter 16, that allows to maximise the sensitivity of the device with respect to the wavelength of the second reflected NIR light beam. After having passed through the second interferential emission filter 16, the second reflected NIR light beam passes through a third lens 17 for imaging that focuses it on a NIR sensor device 18 for imaging, optionally a CCD sensor or a SCMOS sensor.

Optionally, the NIR sensor device 18 is operated at an imaging frequency of at least 100 frames/sec in order to provide a numerical indication of the drift of the position of the eye and to thus calculate from the sequence of the images a tracking of the area under observation, so as to compensate for the angular position data of the excitation light beam.

The Bessel beam generation optical unit 2 of the apparatus according to the invention can advantageously include a static optical phase filter placed on the Fourier plane of the optical launch unit 19 such as a bidimensional grating made of multiple dielectric layers, optionally an axicon lens 21, still more optionally provided with a phase mask 22 as schematically shown in FIGS. 6A and 6B, respectively.

Figure 7A:
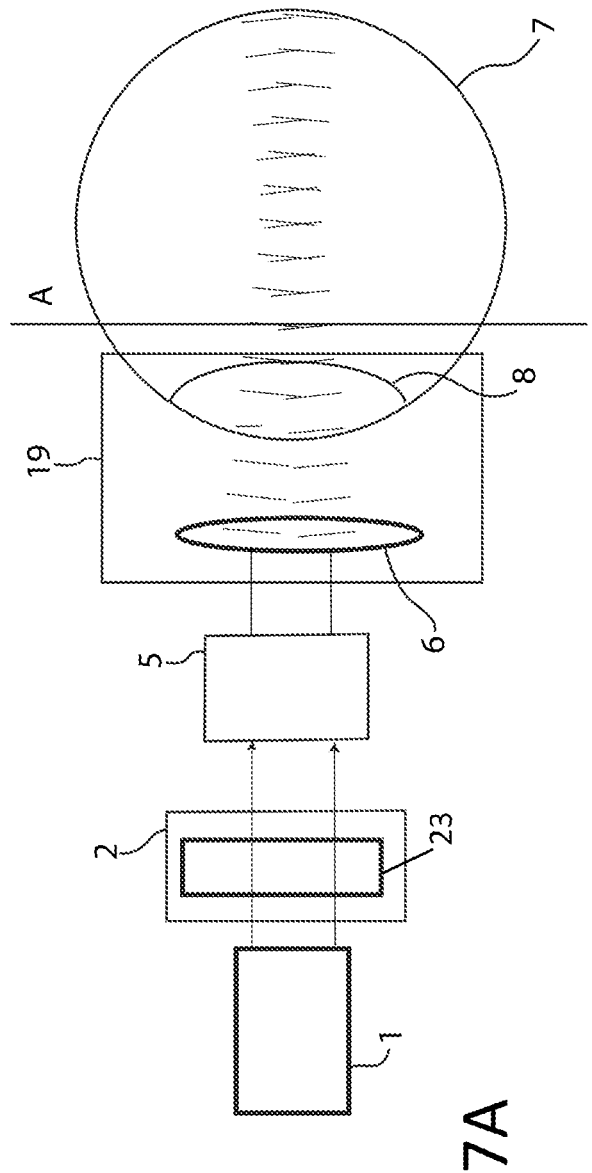
Figure 7B:
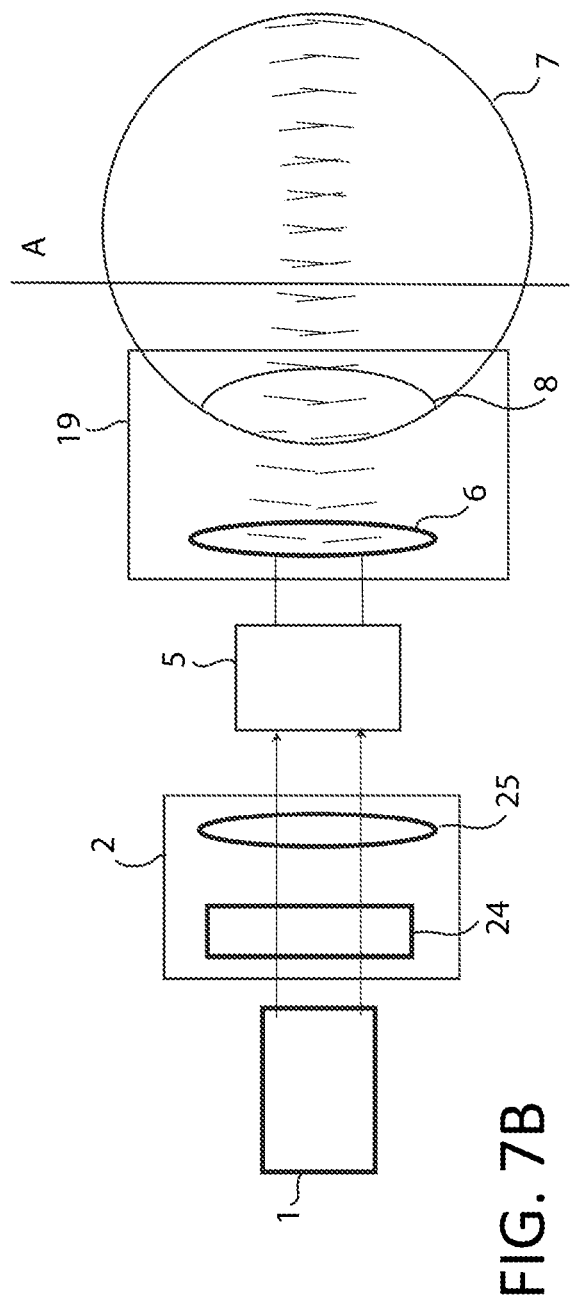

Alternatively, the Bessel beam generation optical unit 2 of the apparatus according to the invention can advantageously include a dynamic optical filter placed on the Fourier plane of the optical launch unit 19 such as a spatial light modulator (SLM) that may be a phase SLM modulator 23 for the beam emitted by the first light source 1 or an amplitude SLM modulator 24 for the beam emitted by the first light source 1 followed by (i.e. positioned upstream of) a Fourier lens 25 that allows to make the Fourier transform of the field of the light beam exiting the SLM modulator 24, as schematically shown in FIGS. 7A and 7B, respectively.

FIGS. 6 and 7 schematically show the composition of the excitation light beam in a Bessel beam in correspondence of a plane A placed between the lens 8 and the fundus of the sample eye 7, optionally placed on the fundus of a sample eye 7, the plane A being orthogonal to the direction of the excitation light beam (i.e., orthogonal to the optical axis, also indicated as z axis).

The scanning system 5 of the apparatus according to the invention can be of a standard type, such as for instance a scanning system with galvanometer mirrors 26 of which FIG. 8A schematically shows an example. In the preferred embodiment, the Bessel beam scanning system 5, schematically shown in FIG. 8B, includes a first and second wedges (wedge filters, indicated by the reference numerals 27 and 28) configured to independently rotate so that the reciprocal displacement of the rotation allows different scanning figures of the sample eye 7. In particular, the property of the two wedges 27 and 28 of the scanning system 5 to independently rotate causes their mutual position and any difference in their rotation speed (in a continuous or stepped way) to allow to make different scanning figures, such as spiral and concentric or pseudo-random circle figures. In the preferred embodiment, the movement of the two wedges 27 and 28 is generated by two separate motors, synchronously controlled with a resolution on the angular position of the two wedges 27 and 28 equal to at least 1/50 of a degree, whereby the scanning resolution is at least one microradian on a field of ±1°. This scanning system 5 allows to minimise the distance between the Bessel beam generation optical system 2 and the external surface of the sample eye 7 (i.e. the outer surface of the cornea) without limiting the numerical aperture of the generation optical system 2 and in particular it allows to make extremely precise scanning for small angles since scanning depends on the angle of the wedges 27 and 28, the refractive index of the glass used and the rotation angle; finally, the lack of reciprocating motion (present in scanning systems with galvanometer mirrors) eliminates vibrations which can reduce quality and precision of the image obtained as a result of the scanning.

The preferred embodiments of this invention have been described and a number of variations have been suggested hereinbefore, but it should be understood that those skilled in the art can make other variations and changes without so departing from the scope of protection thereof, as defined by the attached claims.

The invention claimed is:

1. A fluorescence microscopy apparatus for analysing a fundus of a sample eye of a patient comprising:
    a generation optical unit configured to receive a basic light beam from a first light source and to generate an excitation light beam;
    a scanning system configured to receive the excitation light beam from the generation optical unit and to make the excitation light beam scan at least one portion of the fundus of the sample eye;
    an optical launch unit configured to receive the excitation light beam from the scanning system and to at least partially collimate an isotropic radiation of fluorescent molecules of the sample eye in a fluorescence beam, the optical launch unit comprising an objective having a focal length $f_{obj}$ and an optical power $K_{obj}$ equal to $$K_{obj}=1/f_{obj}$$

where n is a refractive index of the medium;
    a patient's head supporting and positioning unit configured to support the head with cornea and lens of the sample eye facing the optical launch unit and to position the sample eye (7) in a launch position at a distance d from the objective, wherein in the launch position the optical launch unit and cornea and lens of the sample eye form an optical launch assembly having an effective optical power $K_{\mathit{eff}}$ equal to $$K_{\mathit{eff}} = 1/f_{\mathit{eff}} = K_{obj} + K_{eye} - \frac{d}{n_i} \cdot K_{obj} \cdot K_{eye}$$

where $f_{\mathit{eff}}$ is an effective focal length of the optical launch assembly, $K_{eye}$ is a constant optical power contribution, $n_i$ is a refractive index of the medium between sample eye and objective;
    a sensor device configured to detect the fluorescence beam coming from the optical launch unit;
    one or more optical components configured to transmit said excitation light beam coming from the generation optical unit to the scanning system and to transmit said fluorescence beam from the optical launch unit and coming from the scanning system to the sensor device;
        wherein when said patient's head supporting and positioning unit positions the sample eye in the launch position, said optical launch assembly formed by the optical launch unit and the cornea and lens of the sample eye is configured to send the excitation light beam on said at least one portion of the fundus of the sample eye, and the generation optical unit is configured to generate an excitation light beam having phase relationships configured to compose said excitation light beam, after having passed through the optical launch assembly, in a Bessel beam inside the sample eye in correspondence of a plane orthogonal to an optical propagation axis, wherein said plane is between the lens of the sample eye and said at least one portion of the fundus of the sample eye, the focal length $f_{obj}$ of the objective satisfying the condition that an effective numerical aperture $NA_{\mathit{eff}}$ of said optical launch assembly, given by $$NA_{\mathit{eff}}=n_{eye}\cdot\sin(R_{eye}/f_{\mathit{eff}})$$

is not lower than 0.9, where $n_{eye}$ is a refractive index of the sample eye and $R_{eye}$ is the radius of the sample eye.

2. The apparatus according to claim 1, wherein, when said patient's head supporting and positioning unit positions the sample eye in the launch position, the distance d of the sample eye from the objective is not longer than 20 mm, optionally not longer than 10 mm, more optionally not longer than 5 mm, still more optionally not longer than 2 mm.

3. The apparatus according to claim 1, further including at least one first narrowband cleaning filter configured to eliminate a spurious fluorescence background from the excitation light beam.

4. The apparatus according to claim 1, wherein the objective is a single or double adaptive lens.

5. The apparatus according to claim 4, wherein the objective is an adaptive contact lens whereby the distance d of the sample eye from the objective is zero.

6. The apparatus according to claim 1, further comprising an imaging optical unit configured to focus said fluorescence beam on the sensor device.

7. The apparatus according to claim 1, wherein the sensor device includes a plurality of sensing elements selected from the group comprising photomultipliers, avalanche diodes, CCDs, or SCMOSs.

8. The apparatus according to claim 7, including a plurality of microlenses placed upstream of the sensor device each one of which is biunivocally coupled to a respective element of the plurality of sensing elements of the sensor device.

9. The apparatus according to claim 1, including a second light source generating an additional excitation light beam configured to excite at least one additional portion of the sample eye, that internally includes said at least one portion of the sample eye scanned by the excitation light beam generated by the generation optical unit, said additional excitation light beam being configured to saturate an autofluorescence of intraocular tissues of the sample eye.

10. The apparatus according to claim 1, wherein the generation optical unit includes a static optical phase filter placed on the Fourier plane of the optical launch unit.

11. The apparatus according to claim 10, wherein the generation optical unit the static optical phase filter placed on the Fourier plane of the optical launch unit is selected from the group comprising a bidimensional grating made of multiple dielectric layers, an axicon lens, and an axicon lens provided with a phase mask.

12. The apparatus according to claim 1, wherein the generation optical unit includes a spatial light modulator.

13. The apparatus according to claim 12, wherein the spatial light modulator is a phase spatial light modulator or an amplitude spatial light modulator followed by a Fourier lens.

14. The apparatus according to claim 1, wherein the scanning system includes a first and a second wedges configured to independently rotate by means of two separated motors, configured to be controlled in a synchronous way.

15. The apparatus according to claim 14, wherein the first and second wedges have a resolution of angular position equal to at least $1/50$ of a degree, whereby a scanning resolution is equal to at least one microradian on a field of ±1°.

16. The apparatus according to claim 1, including a wide-field imaging system operating in near infrared (NIR) for imaging sub-retinal structures of the sample eye and an additional optical component, placed between the scanning system and the optical launch unit, said additional optical component being configured to be transparent to radiation in near infrared and to reflect the excitation light beam from the scanning system towards the optical launch unit and the fluorescence light beam from the optical launch unit towards the scanning system, the wide-field imaging system further comprising:
a third light source configured to generate a first NIR light beam to be sent to said additional optical component;
a NIR sensor device configured to detect a second NIR light beam reflected by sub-retinal structures of the sample eye and coming from the additional optical component;
one or more NIR optical components configured to transmit said first NIR light beam from the third light source to said additional optical component and said second reflected NIR light beam coming from said additional optical component to the NIR sensor device.

17. The apparatus according to claim 16, wherein the wide-field imaging system further includes an imaging optical unit configured to focus the second NIR light beam on the NIR sensor device.

18. The apparatus according to claim 16, including at least one second narrowband cleaning filter configured to eliminate a spurious fluorescence background from said first NIR light beam.

19. The apparatus according to claim 16, wherein the NIR sensor device is a CCD sensor or a SCMOS sensor.

20. The apparatus according to claim 16, wherein the NIR sensor device is configured to operate at a frequency not lower than 100 frames/sec.

* * * * *